United States Patent
Lansac

(10) Patent No.: US 10,561,499 B2
(45) Date of Patent: Feb. 18, 2020

(54) AORTIC RING AND ANCILLARY DEVICE FOR IMPLANTING IT

(71) Applicant: Assistance Publique—Hopitaux de Paris, Paris (FR)

(72) Inventor: Emmanuel Lansac, Malakoff (FR)

(73) Assignee: Assistance Publique—Hopitaux de Paris, Paris (FR)

( * ) Notice: Subject to any disclaimer, the term of this patent is extended or adjusted under 35 U.S.C. 154(b) by 173 days.

(21) Appl. No.: 15/910,500

(22) Filed: Mar. 2, 2018

(65) Prior Publication Data

US 2018/0185149 A1 Jul. 5, 2018

Related U.S. Application Data

(63) Continuation of application No. 12/940,353, filed on Nov. 5, 2010, now Pat. No. 9,937,040, which is a continuation of application No. 10/912,570, filed on Aug. 6, 2004, now abandoned.

(60) Provisional application No. 60/552,199, filed on Mar. 12, 2004.

(30) Foreign Application Priority Data

Aug. 8, 2003 (FR) ..................................... 03 09794

(51) Int. Cl.
*A61F 2/24* (2006.01)

(52) U.S. Cl.
CPC ............. *A61F 2/2442* (2013.01); *A61F 2/24* (2013.01); *A61F 2/246* (2013.01); *A61F 2/2412* (2013.01); *A61F 2/2427* (2013.01); *A61F 2/2478* (2013.01); *A61F 2/2481* (2013.01); *A61F 2/2409* (2013.01)

(58) Field of Classification Search
CPC ........ A61F 2/24; A61F 2/2412; A61F 2/2427; A61F 2/2442; A61F 2/246; A61F 2/2478; A61F 2/2481; A61F 2/2409
See application file for complete search history.

(56) References Cited

U.S. PATENT DOCUMENTS

| | | | |
|---|---|---|---|
| 5,674,280 | A | 10/1997 | Davidson et al. |
| 5,741,274 | A | 4/1998 | Lenker et al. |
| 5,741,283 | A | 4/1998 | Fahy |
| 6,248,116 | B1 | 6/2001 | Chevillon et al. |
| 6,264,691 | B1 | 7/2001 | Gabbay |
| 6,338,740 | B1 | 1/2002 | Carpentier |
| 6,406,492 | B1 | 6/2002 | Lytle |
| 2004/0054406 | A1 | 3/2004 | Dubson et al. |

(Continued)

FOREIGN PATENT DOCUMENTS

| | | |
|---|---|---|
| CH | 1528459 | 12/1989 |
| FR | 2827756 A1 | 1/2003 |

(Continued)

OTHER PUBLICATIONS

French Patent Office, Search Report in FR 0309794, dated Mar. 24, 2004.

*Primary Examiner* — William H Matthews
(74) *Attorney, Agent, or Firm* — Dorton & Willis, LLP

(57) ABSTRACT

Aortic ring (1) made of a flexible, suturable and biocompatible material, having a length, in the implanted state, making it possible to maintain a normal aortic ring diameter, said ring comprising, or being able to be combined with, means for holding the ring in a closed position in its site of implantation, in particular in a subvalvular plane.

16 Claims, 5 Drawing Sheets

(56) References Cited

U.S. PATENT DOCUMENTS

2005/0075584 A1 4/2005 Cali
2005/0165478 A1 7/2005 Song

FOREIGN PATENT DOCUMENTS

| WO | 9739687 A1 | 10/1997 |
| WO | 9934748 A1 | 7/1999 |

1

AORTIC RING AND ANCILLARY DEVICE FOR IMPLANTING IT

CROSS-REFERENCE TO RELATED APPLICATIONS

This application is a continuation of U.S. patent application Ser. No. 12/940,353, filed Nov. 5, 2010 now U.S Pat. No. 9,937,040 which is a continuation of U.S. patent application Ser. No. 10/912,570, filed Aug. 6, 2004 (abandoned) which claims the benefit of U.S. Provisional Application Ser. No. 60/552,199, filed Mar. 12, 2004 (expired), which claims the priority of French Application No. 0309794, filed Aug. 8, 2003 (now French Patent No. 2858543), the disclosures of which are hereby incorporated by reference herein.

TECHNICAL FIELD

The present invention relates to an artificial aortic ring intended to reduce or contain the normal aortic ring in a number of diseases of the cardiac valves. The invention also relates to ancillary devices and methods for implanting this ring.

BACKGROUND

The natural aortic ring is a fibromuscular structure which is able to expand in each cardiac cycle. It has a sigmoid shape made up of three commissural summits and three nadirs corresponding to the point of insertion of the aortic valvules.

Insufficiency of the aortic valvules generally requires reparative surgery. This is particularly so in the case of dystrophic valvular insufficiency, for example annuloaortic ectasia, isolated valvular dysplasia, or bicuspid aortic valve disease.

SUMMARY

The present invention proposes to reduce or contain, when necessary, the diameter of the aortic ring, in a subvalvular and/or supravalvular position, especially in the case of dystrophic aortic valve insufficiency, or in the case of aortic valve replacement by means of a valve with no reinforcement, making it necessary to contain the ring in a subvalvular and/or supravalvular position.

Among these valve insufficiencies, a distinction will be made between those involving lesions of the valvules, in particular acute articular rheumatism, endocarditis, and traumatic tears, and those without valvular lesion and with bicuspid or tricuspid valves which are macroscopically normal, especially annuloaortic ectasia, isolated valvular dysplasia, bicuspid aortic valve disease, and Laubry-Pezzi syndrome.

The subject of the invention is an aortic ring made of a flexible, suturable and biocompatible material, sterile or sterilizable, having a height preferably at least equal to 2 mm and having a length, in the implanted state, making it possible to maintain a normal aortic ring diameter, said ring comprising, or being able to be combined with, means for holding the ring in a closed position in its site of implantation.

The dimensions of the ring are advantageously such that the ring can be implanted around the aortic root, and in a subvalvular position.

The height of the ring according to the invention is advantageously greater than 1 mm and preferably between 2 and 4 mm. The choice of height of the ring can of course be tailored to the size and physiology of the patient.

The ring can comprise closure means.

Thus, in a particular embodiment, it can be made from the outset in a closed ring shape, in cases in particular where the surgical intervention involves complete resection of an aortic segment, permitting placement of a ring that is initially closed.

In another embodiment, these means can comprise means of closure or of fastening which are already in place, allowing a ring which is initially open to be formed into a circle and closed at both ends. These means can be staples or threads, for example, initially engaged in the ring, or any other means of closure.

Finally, the ring according to the invention can also be in the open form of a band which initially has no means of closure, this closure being able to be achieved, for example, by suturing.

In the case of a ring which is initially closed, it is advantageous to provide sets of rings of different heights and different diameters. However, it is also possible to conceive of having just one height with different diameters and of allowing the surgeon to reduce the height to the desired value by cutting the circular ring.

In the case of a ring which is initially open, the ring is advantageously in the form of a band whose two ends will be able to be joined together after placement around the aortic segment to be reduced or contained. In this case too, it is possible to provide either a set of bands of different heights and/or lengths, or a ring which in the band state has a maximum length, and the ends of the ring which protrude after closure can be eliminated by cutting either before or after implantation.

The ring according to the invention is made of a flexible, suturable and biocompatible material. This material, which must obviously be sterile, is preferably produced in a textile form permitting straightforward fixation by suturing and/or closure of the ring, for example by a thread. The material used is preferably polytetrafluoroethylene, for example in woven form, although other biocompatible materials can be used, such as, for example, Dacron. The person skilled in the art presently uses vascular prostheses made of Dacron or of polytetrafluoroethylene, and these materials are well known to him.

In a refined embodiment, the material can be elastic so as to exert a pressure which makes it possible to reduce the aortic diameter in the diastolic phase, respecting the physiology of the normal aortic ring, while expanding for an increase in systolic diameter. In this case, the variation in diameter is preferably limited to a less than 10% increase in diameter of the prosthetic ring for a pressure greater than 140 mmHg. For expandable rings, use will be made of, for example, polytetrafluoroethylene or silicone.

Preferably, the ring according to the invention can exist in three sizes defined by the diameter of the ring. A first size is advantageously of the order of 23 mm, the second of the order of 25 mm, and the last of the order of 27 mm.

In the case of an expandable ring, the increase in diameter in each of these cases is preferably limited to a maximum of 2 mm.

The cross section of the ring can be analogous to that of the cut of a fabric having a thickness for example of between 2 and 4 mm. However, any other shape of cross section can be provided, for example oval or others, formed for example by knitting.

The invention also relates to the use of a ring made of a flexible, suturable and compatible material, having a height preferably at least equal to 2 mm and preferably of between 2 and 4 mm, initially open or closed, for production of an aortic ring, said aortic ring having in particular the characteristics listed above, and said aortic ring comprising or being combined with means for holding the ring in a closed position in its site of implantation, in particular in a subvalvular position or possibly also in a supravalvular position.

The invention also relates to an ancillary device for implanting an aortic ring according to the invention and comprising an annular frame or open arc optionally connected, preferably in a detachable manner, to a rod which is substantially transversal with respect to the plane of the ring or of the arc, means being provided to hold the aortic ring according to the invention along this frame or arc in a position which is such that, when suturing the aortic ring around the aorta, the aortic ring cannot locally fold or pucker during suturing. An ancillary device having the shape of an open arc can be used when the aortic ring according to the invention is implanted in a subvalvular position without separation of the coronary vessels.

The means for fixing the aortic ring on the ancillary device can be of different types, for example a system of foldable tabs or other fixing means holding the aortic ring against the frame. Alternatively, this fixing can be effected by one or more threads connected to the frame and holding the aortic ring along this frame without any possibility of puckering or folding, such a thread being able to be released subsequently, for example by sectioning.

The invention also relates to a method of implanting an aortic ring according to the invention.

This method involves positioning the ring around and outside the natural or artificial aortic wall.

According to a first mode of implementation, the method involves performing an aortic subvalvular annuloplasty by placing and implanting the ring in a circular plane below the nadir of each sigmoid valve. The ring is preferably fixed by U-shaped stitches, for example five to six uniformly spaced stitches, which are passed from the inside outward.

For example, in the case of an aneurysm of the aortic root, the method consists in replacing the aortic root with a tubular implant, for example of Dacron, indented with three Valsalva neo-sinuses, combined with aortic subvalvular annuloplasty round the subvalvular base of the reconstituted wall, before reinsertion of the coronary vessels.

In a second mode of implementation, which moreover can be combined with the first one, the method involves performing supravalvular annuloplasty, at the level of the sinotubular junction by implantation of the ring, preferably using commissural U-shaped stitches passed from the inside outward, for example three stitches.

For example, particularly in cases of isolated valvular dysplasia without aneurysm of the aortic root, subvalvular annuloplasty and supravalvular annuloplasty are performed, conserving the native aortic root, the two rings being disposed at the two aforementioned locations.

Other advantages and characteristics of the invention will become clear on reading the following description based on a nonlimiting example and with reference to the attached drawing, in which:

DETAILED DESCRIPTION

Figure 1:
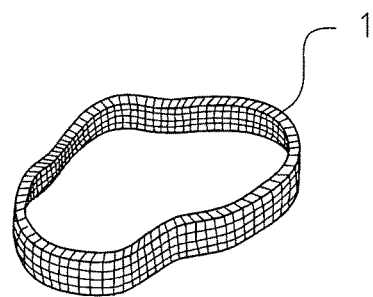
FIG. 1 shows a diagrammatic view of a closed ring according to the invention.

Reference is first made to FIG. 1.

FIG. 1 shows a ring made of Dacron (trademark), this ring 1 being made of flexible Dacron in the form of an impermeable knit which is usual in vascular surgery.

In the circular state, this ring has a diameter of 23, 25 or 27 mm depending on the size of the ring. The height of the ring is 2 mm.

This ring can be fitted in place after total resection, permitting separation of the aorta, for engagement around the remaining segment.

Figure 2:
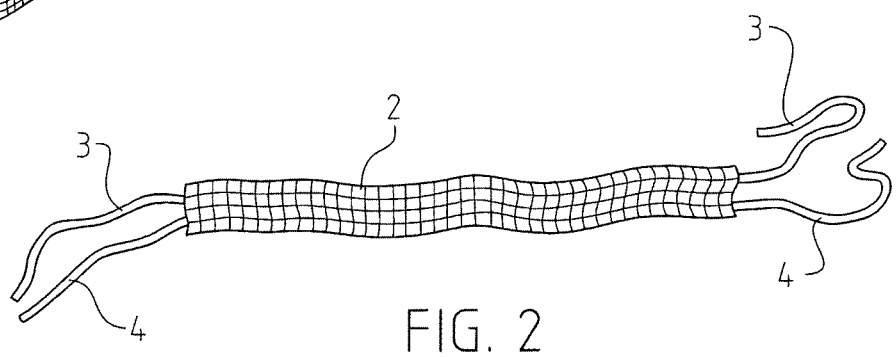
FIG. 2 shows a diagrammatic view of a ring which is initially open.

FIG. 2 shows a ring which is initially open and in the form of a band 2 made of the same material as in FIG. 1, and having a length equivalent to the perimeter of the circle corresponding to the desired diameter. By way of example, this ring has two threads 3, 4 passed through it and emerging at both ends in order to permit closure by a knot.

This closure device can be replaced by any other closure device which is strong and biocompatible, for example clips or fasteners.

The band can also be without a thread and can then be closed using knots of non-absorbable suture thread or the like.

The length of the band can be .pi.D, D being the diameter, for example one of the aforementioned diameters.

The band can also be of greater length, particularly in the case where it does not have ready fastening means, so as to allow it to be cut to the length desired by the surgeon.

Reference is now made to FIGS. 3 through 9 which show a ring being implanted in an operation involving supravalvular aortic conservation and subvalvular annuloplasty.

Figure 3:
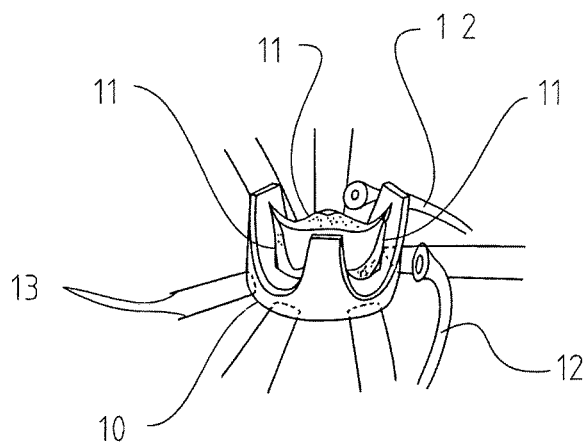
FIGS. 3 through 7 show diagrammatic views of different steps in implanting an aortic ring according to the invention in a procedure involving supravalvular conservation combined with subvalvular annuloplasty.

FIG. 3 shows the native root 10 of the aorta after resection of the three Valsalva sinuses, revealing the three sigmoid valves 11. The coronary vessels 12 have been detached. Six U-shaped threads 13 have been placed in a circular plane below the nadir of the sigmoid valves 11, these six threads being in standby to receive the aortic ring.

Figure 4:
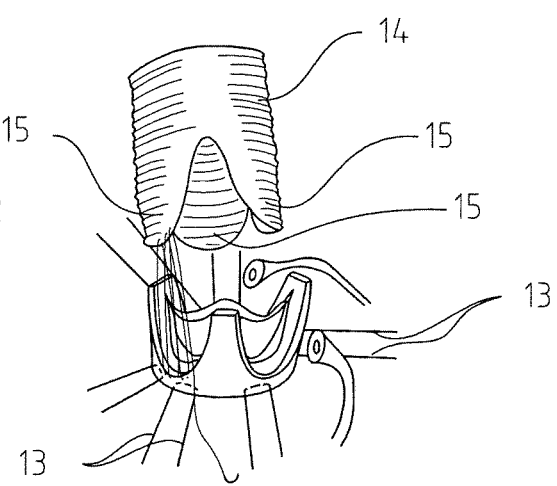

As will be seen in FIG. 4, a prosthesis 14 is then presented for replacement of the ascending aorta, said prosthesis being made of Dacron and indented to form three Valsalva neo-sinuses 15.

Figure 5:
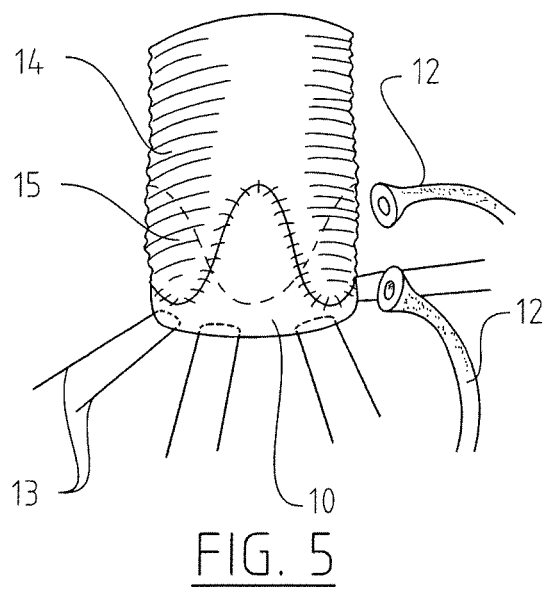

In FIG. 5, the prosthesis 14 has been implanted and sutured.

Figure 6:
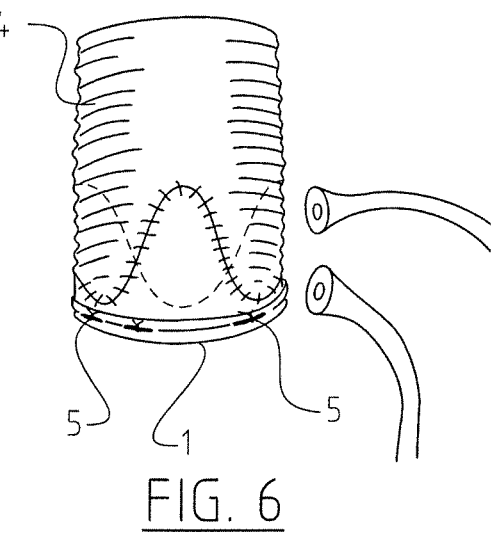

In FIG. 6, the surgeon has now engaged, and lowered onto the ascending aortic prosthesis 14, an initially closed aortic ring 1 which is then secured around the aortic root, at the location marked by the threads 13 which are passed through the ring 1, drawn and tightened to form knots 5.

Figure 7:
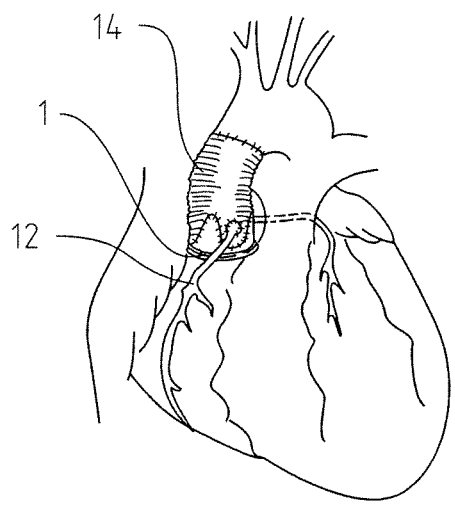

FIG. 7 shows the result once the operation has been completed. The coronary vessels 12 have been reinserted at two of the competent neo-sinuses 15, and the continuity of the aorta has been re-established at the upper end of the prosthesis 14.

Figure 9:
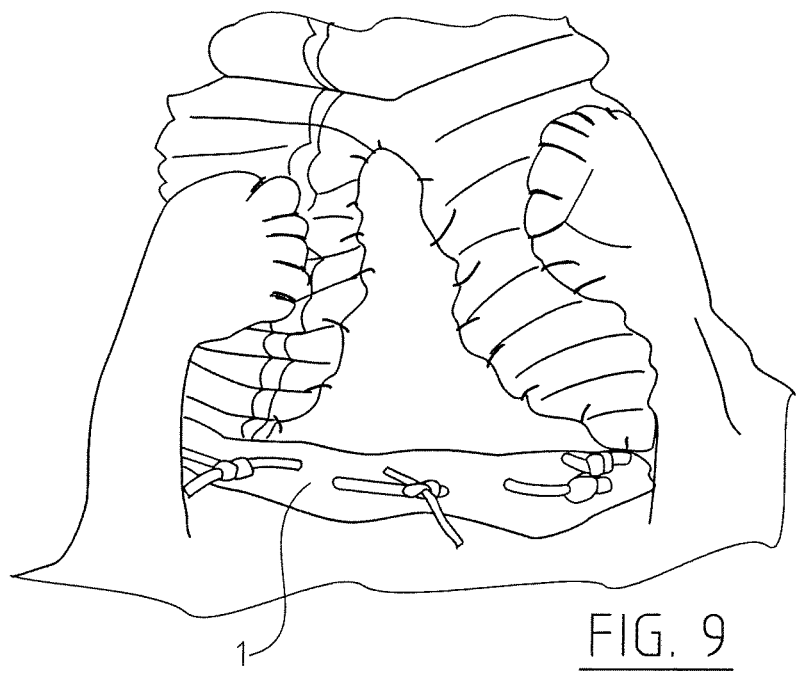
FIG. 9 shows a diagrammatic view at the stage in FIG. 7, showing the detailed implantation of the ring.

FIG. 9 illustrates the end of the phase of descent of the aortic ring and its fixation, then reinsertion of the coronary vessels.

Figure 8:
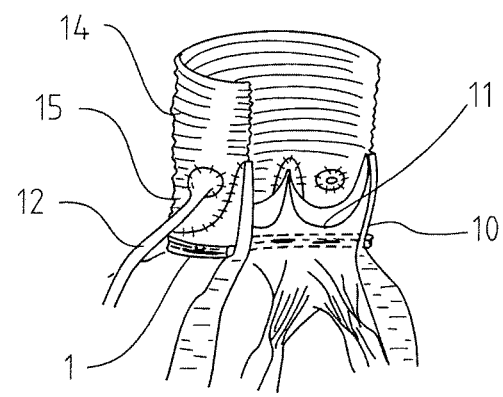
FIG. 8 shows a view of the result after longitudinal opening of the aortic root to permit better understanding.

An anatomical view has been shown in FIG. 8, illustrating the position of the aortic ring 1 situated in a plane corresponding to the root of the aorta and below the nadir of the sigmoids.

By virtue of the invention, it has thus been possible, by means of the subvalvular annuloplasty achieved by the aortic ring 1, to strengthen the aortic root and maintain its diameter during the diastolic phase. The valve function has thus been re-established without any intervention of the valves themselves.

Figure 10:
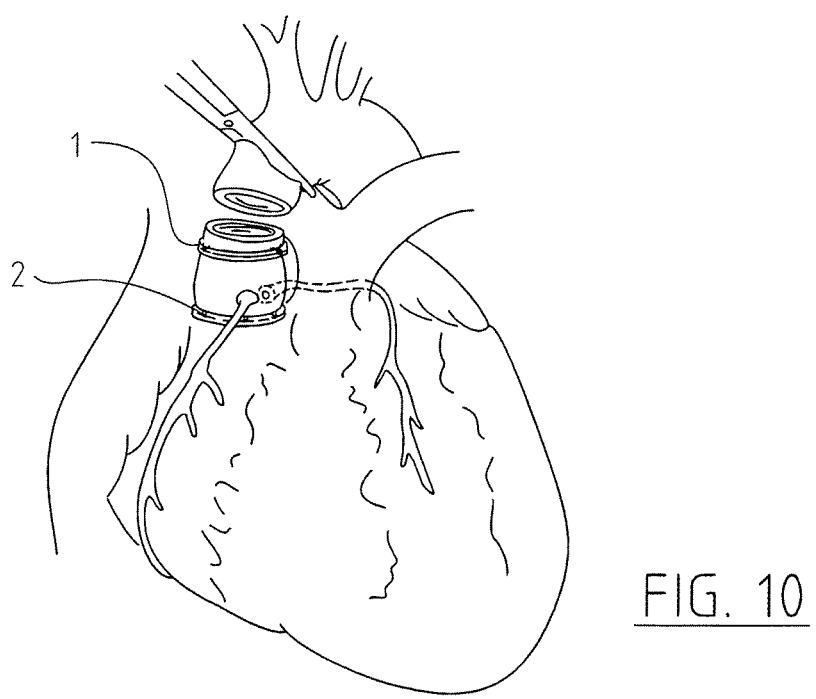
FIG. 10 shows a diagrammatic view during surgery in the context of supravalvular and subvalvular aortic annuloplasty, with conservation of the native aortic root.
Figure 11:
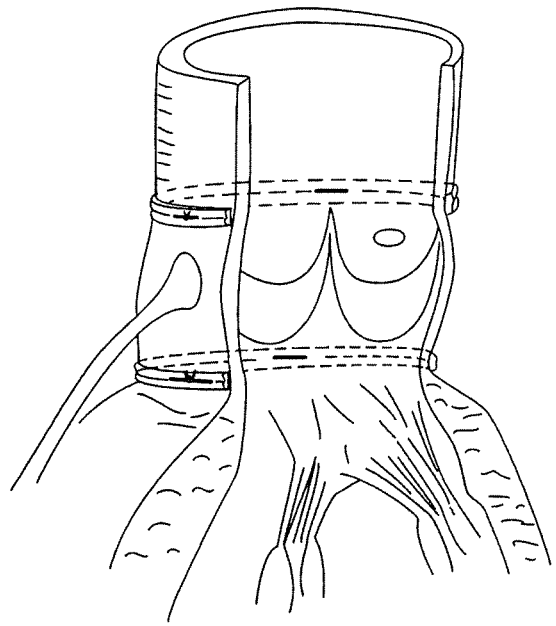
FIG. 11 shows a view at the same stage after longitudinal opening of the aortic root to permit better understanding.

Referring to FIG. 10, this shows the position occupied by rings, namely a subvalvular ring 2 and a supravalvular ring 1 in the case of valve repair with conservation of the native aortic root, or in the case of a valve replacement without reinforcement.

The subvalvular position of the ring 2 corresponds substantially to the position shown in FIGS. 4 and 5. Only the implantation technique varies. This is a ring which is initially open and is passed under the coronary ostia without these being detached from the native aortic root.

The supravalvular ring 1 surrounds the three sites of commissural implantation of the sigmoid valves.

In practice, the two rings can be placed on aorta ends and/or implants completing the aorta and restoring the sinuses.

Figure 12:
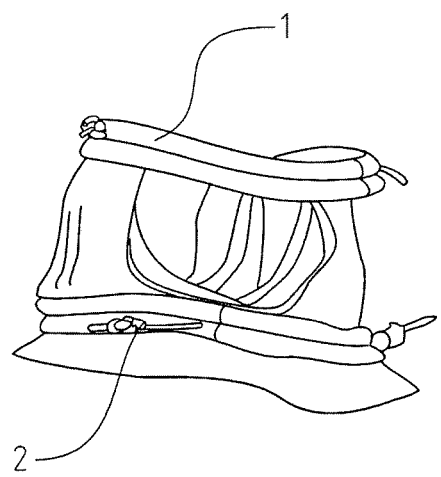
FIG. 12 shows a view similar to that in FIG. 11, but after resection of the native Valsalva sinuses.

FIG. 12 shows an anatomical view of these implantations, with resection of the native Valsalva sinuses.

Figure 13:
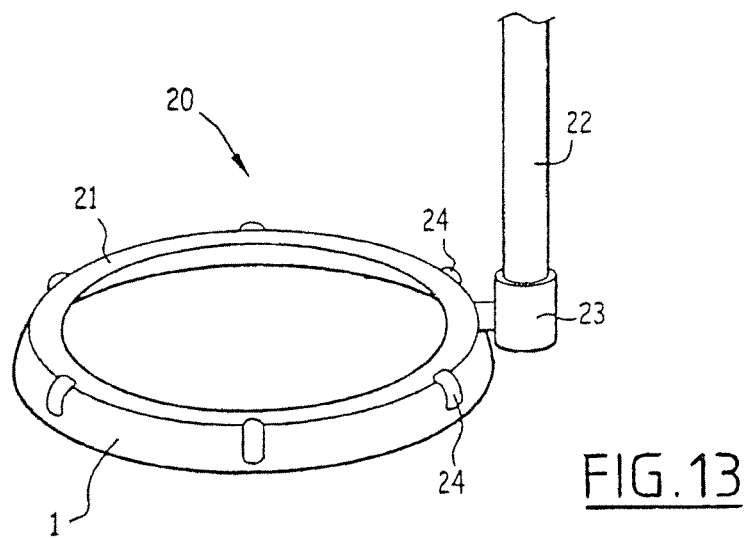
FIG. 13 shows a diagrammatic view of a first ancillary device for implanting the aortic ring.

Referring to FIG. 13, this shows an ancillary device 20 intended to facilitate the implantation and suturing of an aortic ring 1 so as to avoid the risks of malpositioning and folding of the ring. This ancillary device 20 comprises a rigid or semi-rigid frame 21 having substantially the diameter of the aortic ring 1 and being fixed to the end of a handle 22, preferably via a removable fixing means 23. The ring 1 is positioned under the annular part 21 and is held against the latter by foldable tabs 24 spaced at regular intervals.

The surgeon takes the assembly consisting of ancillary device and ring and lowers it to the desired position, for example the subvalvular position shown in FIG. 7 or the supravalvular position shown in FIG. 10. Once the assembly is in place, he releases the handle 22 and the fixing device 23 then proceeds to suture the ring 1 in position, said ring being prevented from moving or folding by virtue of the presence of the annular frame 21. At the end of implantation of the ring, the surgeon deploys the arms 24 and withdraws the frame.

Figure 14:
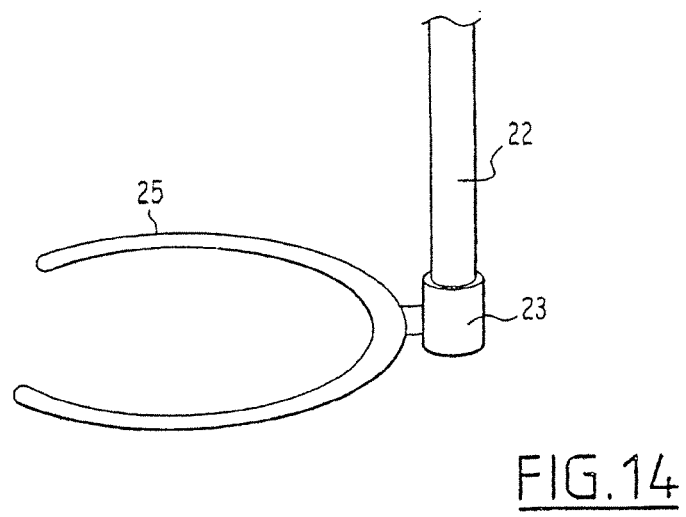
FIG. 14 shows a view of a modified ancillary device.

FIG. 14 shows another embodiment of an ancillary device, this time comprising a rigid or semi-rigid frame in the form of an open arc 25, which is preferably deformable. A ring 2, which is initially open, is fixed in place under the arc 25 by means of foldable arms 24 or any other fixing means, for example with the aid of threads that have been drawn tight. The assembly formed by the initially open ring and the frame 25 is mounted around the aortic root by passing the frame 25 with its ring, by rotation, under the coronary vessels, without detachment of these. After suturing of the ring, then release of the arc 25, the latter can be disenagaged from the coronary vessels, by reverse rotation, and withdrawn.

The invention claimed is:

1. A method for surgical repair of an aortic valve of a patient, the aortic valve being exposed to alternating diastolic and systolic phases of a cardiac cycle, the aortic valve having a valve axis and contained within a generally tubular aortic root with an inner surface and an outer surface, the aortic valve including a plurality of valve leaflets, the valve leaflets attached to a sigmoid-shaped valve annulus and each having a leaflet free margin, the sigmoid-shaped valve annulus extending circumferentially around the valve axis, the sigmoid-shaped valve annulus extending in height along the valve axis between a nadir portion at a base of the aortic root and a spaced away commissure portion generally at a sinotubular junction of the aortic root, the aortic root also having a subvalvular region located generally below the nadir portion and a supravalvular region located generally above the commissure portion, the aortic root having coronary arteries attached thereto between the subvalvular and supravalvular regions, the aortic root and the valve annulus expanding outwardly away from the valve axis during a cardiac cycle transition from the diastolic phase to the systolic phase and retracting inwardly toward said valve axis during a transition from the systolic phase to the diastolic phase, the valve leaflets movable between a closed configuration in which the leaflet free margins are in an approximated spatial relationship during the diastolic phase and an open configuration in which the leaflet free margins are spaced away from one another during the systolic phase to allow blood flow through the aortic valve generally along a direction parallel to the valve axis, the method comprising:

implanting a subvalvular aortic ring externally on the outer surface and around the aortic root to form a subvalvular closed-perimeter flexible structure around the subvalvular region externally of the aortic root, generally adjacent the nadir portion of the valve annulus and below the attachment points of the coronary arteries;

implanting a supravalvular aortic ring externally on the outer surface and around the aortic root to form a supravalvular closed-perimeter flexible structure around the supravalvular region externally of the aortic root, generally adjacent the commissure portion of the valve annulus and above the attachment points of the coronary arteries; and constraining the aortic root with the subvalvular and supravalvular closed-perimeter flexible structures to an anatomically representative geometry that improves coaptation of the leaflet free margins in the diastolic phase of the cardiac cycle.

2. The method of claim 1, wherein the subvalvular aortic ring is configured as an elongate elastic band having a first end and a second end and a ring closure structure, the ring closure structure operative to join said first and second ends to form the subvalvular closed-perimeter flexible structure, and implanting the subvalvular aortic ring further includes:

inserting the elastic band below the attachment points of the coronary arteries; and joining the first and second ends of the elastic band with the ring closure structure to form the subvalvular closed perimeter flexible structure positioned externally around the aortic root at the subvalvular region.

3. The method of claim 2, wherein the supravalvular aortic ring is elastic and expandable, and the method further comprises:

allowing the elastic supravalvular aortic ring to move between a first supravalvular ring configuration in which the aortic root is exposed to the diastolic phase and a second supravalvular ring configuration of larger annular perimeter than the first supravalvular ring configuration in which the aortic root is exposed to the systolic phase, whereby in the second supravalvular ring configuration the supravalvular aortic ring improves the blood flow through the aortic valve by allowing a controlled expansion of the sinotubular junction of the aortic root as the leaflet free margins move apart during the systolic phase.

4. The method of claim 3, wherein the supravalvular aortic ring includes a silicone member that provides the elasticity to the supravalvular aortic ring.

5. The method of claim 3, wherein the supravalvular aortic ring undergoes an expansion of about 10% when moving from the first supravalvular ring configuration to the second supravalvular ring configuration.

6. The method of claim 2, wherein the subvalvular aortic ring is elastic and expandable, and the method further comprises:
allowing the elastic subvalvular aortic ring to move between a first subvalvular ring configuration in which the aortic root is exposed to the diastolic phase and a second subvalvular ring configuration of larger annular perimeter than the first subvalvular ring configuration in which the aortic root is exposed to the systolic phase, whereby in the second subvalvular ring configuration the subvalvular aortic ring improves the blood flow through the aortic valve by allowing a controlled expansion of the base of the aortic root as the leaflet free margins move apart during the systolic phase.

7. The method of claim 6, wherein the supravalvular aortic ring is elastic and expandable, and the method further comprises:
allowing the elastic supravalvular aortic ring to move between a first supravalvular ring configuration in which the aortic root is exposed to the diastolic phase and a second supravalvular ring configuration of larger annular perimeter than the first supravalvular ring configuration in which the aortic root is exposed to the systolic phase, whereby in the second supravalvular ring configuration the supravalvular aortic ring improves the blood flow through the aortic valve by allowing a controlled expansion of the sinotubular junction of the aortic root as the leaflet free margins move apart during the systolic phase.

8. The method of claim 6, wherein the subvalvular aortic ring includes a PTFE member that provides elasticity to the subvalvular aortic ring.

9. The method of claim 6, wherein the subvalvular aortic ring undergoes an expansion of about 10% when moving from the first subvalvular ring configuration to the second subvalvular ring configuration.

10. The method of claim 2, wherein implanting the subvalvular aortic ring further comprises:
evaluating the native aortic root geometry and selecting a predetermined length of the elongate elastic band based on the native aortic root dimensions.

11. The method of claim 2, wherein the closure structure further comprises a suture and the method further comprises:
suturing the first and second ends of said band together with the suture to provide the subvalvular closed-perimeter flexible structure.

12. The method of claim 2, wherein the closure structure further comprises a flexible wire member on the first and second ends of the elastic band and the method further comprises:
attaching the flexible wire members together to provide the subvalvular closed-perimeter flexible structure.

13. The method of claim 2, wherein the closure structure further comprises a stapling member and the method further comprises:
stapling the first and second ends of the elastic band together with the stapling member to provide the subvalvular closed-perimeter flexible structure.

14. The method of claim 2, further comprising:
compliantly guiding the subvalvular aortic ring around the aortic root, below the attachment points of the coronary arteries.

15. The method of claim 1, wherein the steps of implanting the subvalvular and supravalvular aortic rings further comprise:
placing a plurality of U-stitches through the aortic root to secure the subvalvular aortic ring and supravalvular aortic ring in position externally around the aortic root.

16. The method of claim 1, wherein either of the subvalvular or supravalvular aortic rings further comprises a textile element and the method further comprises:
suturing either of the said subvalvular and supravalvular aortic rings to the aortic root through the textile element.

* * * * *